United States Patent [19]

Jessel, Jr. et al.

[11] Plant 4,506

[45] Feb. 26, 1980

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 963,852

[22] Filed: Nov. 27, 1978

[51] Int. Cl.[2] ..... A01H 5/00
[52] U.S. Cl. ..... Plt./78
[58] Field of Search ..... Plt./78–79

*Primary Examiner*—Robert E. Bagwill
*Attorney, Agent, or Firm*—Donald D. Jeffery

[57] ABSTRACT

A new chrysanthemum plant known by the cultivar name Pot O'Gold and particularly characterized as to uniqueness by the combined characteristics of incurved capitulum form; decorative capitulum type; bronzy yellow ray floret color; diameter across face of capitulum ranging from 100 to 125 mm. at maturity; uniform eight week flowering response period; short plant height, and semi-upright branching pattern.

17 Drawing Figures

1

The present invention comprises a new and distinct cultivar of *Chrysanthemum morifolium*, Ramat., hereinafter referred to by the cultivar name Pot O'Gold.

Pot O'Gold is a product of a planned breeding program which had the objective of creating new chrysanthemum cultivars with incurved inflorescence form, with seven or eight week flowering response, with yellow or bronze inflorescence color, and with the ability to produce commercially acceptable quality in year round pot mum programs. Such traits in combination were not present in previously available commerical cultivars.

Pot O'Gold was originated from a cross made in a controlled breeding program in Barberton, Ohio in 1972. The female parent was #67491005 (unnamed seedling), a yellow incurved decorative originated by the present inventors from a cross between Neptune (unpatented; commercially available) and #57816001 (unnamed seedling). The male parent of Pot O'Gold was Wildfire (U.S. Plant Pat. No. 3,236), a bronze standard. Wildfire and Nepture are products of the breeding programs of the present inventors. The parentage of #57816001 is unknown to the present inventors.

Pot O'Gold was discovered and selected as one flowering plant within the progeny of the stated cross by Walter H. Jessel, Jr. and William E. Duffett on Mar. 25, 1973 in a controlled environment in Barberton, Ohio.

The first act of asexual reproduction of Pot O'Gold was accomplished when vegetative cuttings were taken from the initial selection in May, 1973 in a controlled environment in Barberton, Ohio by a technician working under formulations established and supervised by Walter H. Jessel, Jr. and William E. Duffett. Horticultural examination of selected units initiated Mar. 14, 1974 has demonstrated that the combination of characteristics as herein disclosed for Pot O'Gold are firmly fixed and are retained through successive generations of asexual reproduction.

Pot O'Gold has not been observed under all possible environmental conditions. The phenotype may vary significantly with variations in environment such as temperature, light intensity, and daylength. The following observations, measurements, and comparisons describe plants grown in Barberton, Ohio and in Salinas, Calif. under greenhouse conditions which approximate those generally used in commercial practice.

2

The following traits have been repeatedly observed and are determined to be basic characteristics of Pot O'Gold which in combination distinguish this chrysanthemum as a new and distinct cultivar:

(1) Incurved capitulum form, reflexing at full maturity.

(2) Decorative capitulum type.

(3) Bronzy yellow ray floret color.

(4) Diameter across face of capitulum ranging from 100 to 125 mm. at maturity.

(5) Uniform 8 week flowering response to short days.

(6) Short plant height (requiring two to three long day weeks prior to pinch and short days and one application 2500 ppm B-9 Sp 14 to 21 days after the beginning of short days to attain a flowered plant height of 30 to 45 cm. for May through October flowerings).

(7) Semi-upright branching pattern.

The accompanying photographic drawings show typical inflorescence and foliage characteristics of Pot O'Gold, with the colors being as nearly true as possible with illustrations of this type.

Sheet 1 is a color photograph of Pot O'Gold.

Sheet 2 is a black and white photograph showing three views of the inflorescence of Pot O'Gold.

Sheet 3 is a black and white photograph showing the foliage of Pot O'Gold at three stages of growth.

Of the many commercial cultivars known to the present inventors, the most similar existing cultivar in comparison to Pot O'Gold is Wild Honey (U.S. Plant Pat. No. 3,359), a sport of the maternal cultivar Wildfire. Reference is made to attached Chart A which compares certain characteristics of Pot O'Gold to those same characteristics of Wild Honey. It will be noted that Pot O'Gold has more bronze ray floret color, less incurved capitulum form, smaller diameter across face of capitulum, shorter plant height, and shorter flowering response than Wild Honey. The capitulum type of Pot O'Gold is similar to that of Wild Honey.

In the following description, color values demarked by (a) refer to A Limit Color Cascade (by Munsell, 1972 edition) and such color values were determined between 9:00 and 9:30 A.M. on June 17, 1977 under 150 foot-candle light intensity at Barberton, Ohio. Color values demarked by (b) refer to The Royal Horticultural Society Colour Chart and were determined between 11:00 and 11:30 A.M. on Oct. 20, 1977 under 75 foot-candle light intensity at Salinas, Calif.

Botanical classification: *Chrysanthemum morifolium,* Ramat., cv Pot O'Gold

I. INFLORESCENCE

A. Capitulum (See sheets 1 and 2 of photographic drawings):

*Form.*—Incurved, reflexing with age.

*Type.*—Decorative.

*Permanence.*—14 to 18 days.

*Diameter across face.*—100 to 125 mm.

B. Corolla of ray florets:

*Color (abaxial).*—30-13 streaked over 27-8, oxidizing to 28-11 streaked lightly over 27-4 (a).

*Color (adaxial).*—27-8 streaked lightly over 27-4 to 27-3(a).

*Persistence.*—Resists shatter.

C. Reproductive organs:

*Androecium.*—Present disc florets only; scant to few; scant pollen.

*Gynoecium.*—Present both ray and disc florets.

II. PLANT

A. General appearance: semi-upright branching pattern; short height.

B. Foliage (See sheets 1 and 3 of photographic drawings):

*Color (abaxial).*—Approximately 136A to 136B (b).

*Color (adaxial).*—Approximately 137B to 137C (b).

CHART A

COMPARISON OF POT' GOLD AND WILD HONEY

| Cultivar | Ray Floret Color | Capitulum Form and Type | Diameter Across Face Capitulum | Plant Height | Flowering Response Period |
|---|---|---|---|---|---|
| Pot O' Gold | Golden Bronze to Golden Yellow | Incurved Standard | 100 to 125 mm. | Short | 8 week |
| Wild Honey | Golden Yellow | Semi-Incurved Standard | 130 to 145 mm. | Tall | 9 week |

COMPARISONS MADE OF PLANTS GROWN AS DISBUD PINCHED PLANTS GROWN IN SALINAS, CALIFORNIA AND BARBERTON, OHIO.

We claim:

1. A new and distinct cultivar of *Chrysanthemum morifolium,* Ramat., plant known by the cultivar name Pot O'Gold and particularly characterized as to uniqueness by the combined characteristics of incurved capitulum form, reflexing at full maturity; decorative capitulum type; bronzy yellow ray floret color; diameter across face of capitulum ranging from 100 to 125 mm. at maturity; uniform 8 week flowering response; short plant height; and semi-upright branching pattern.

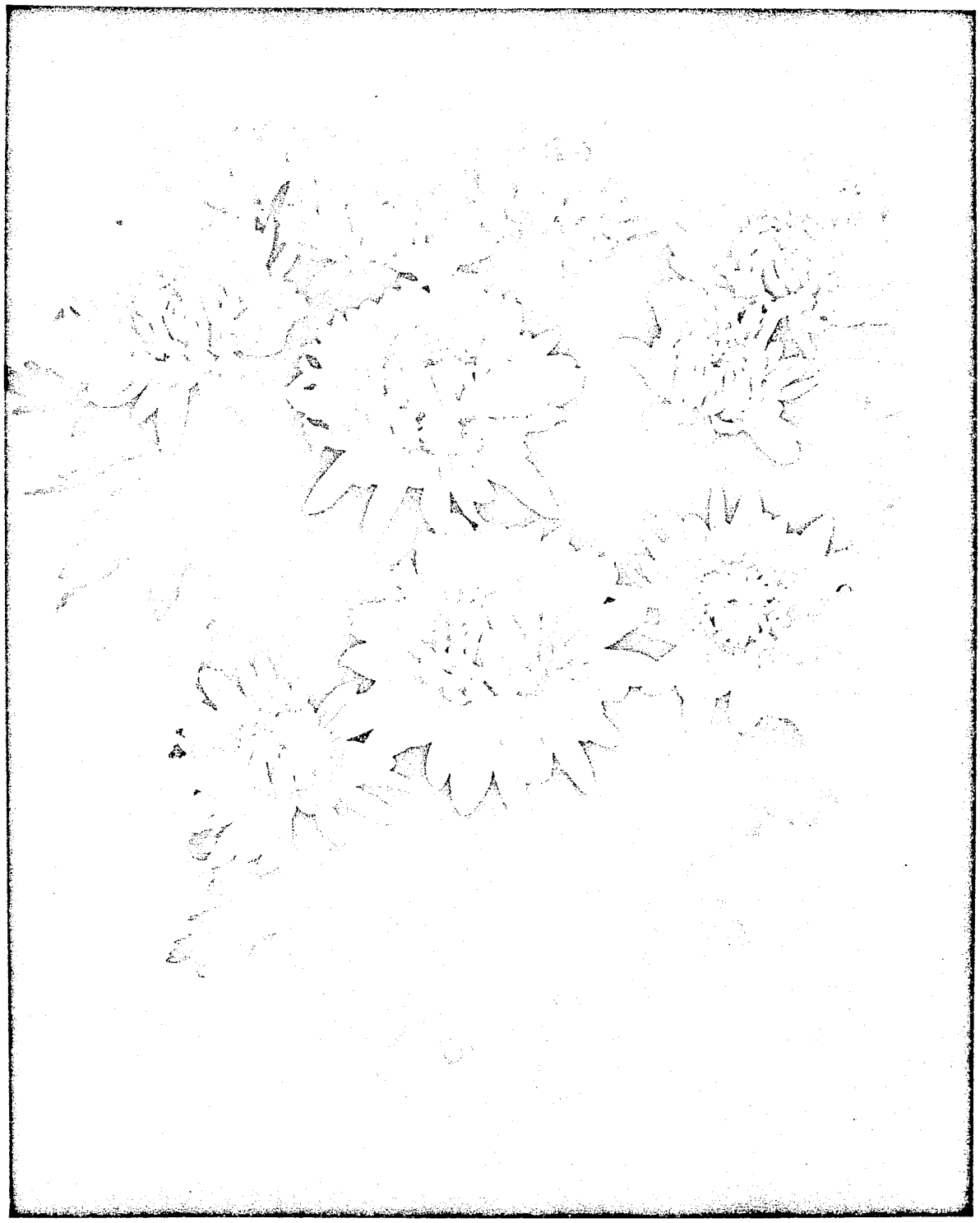

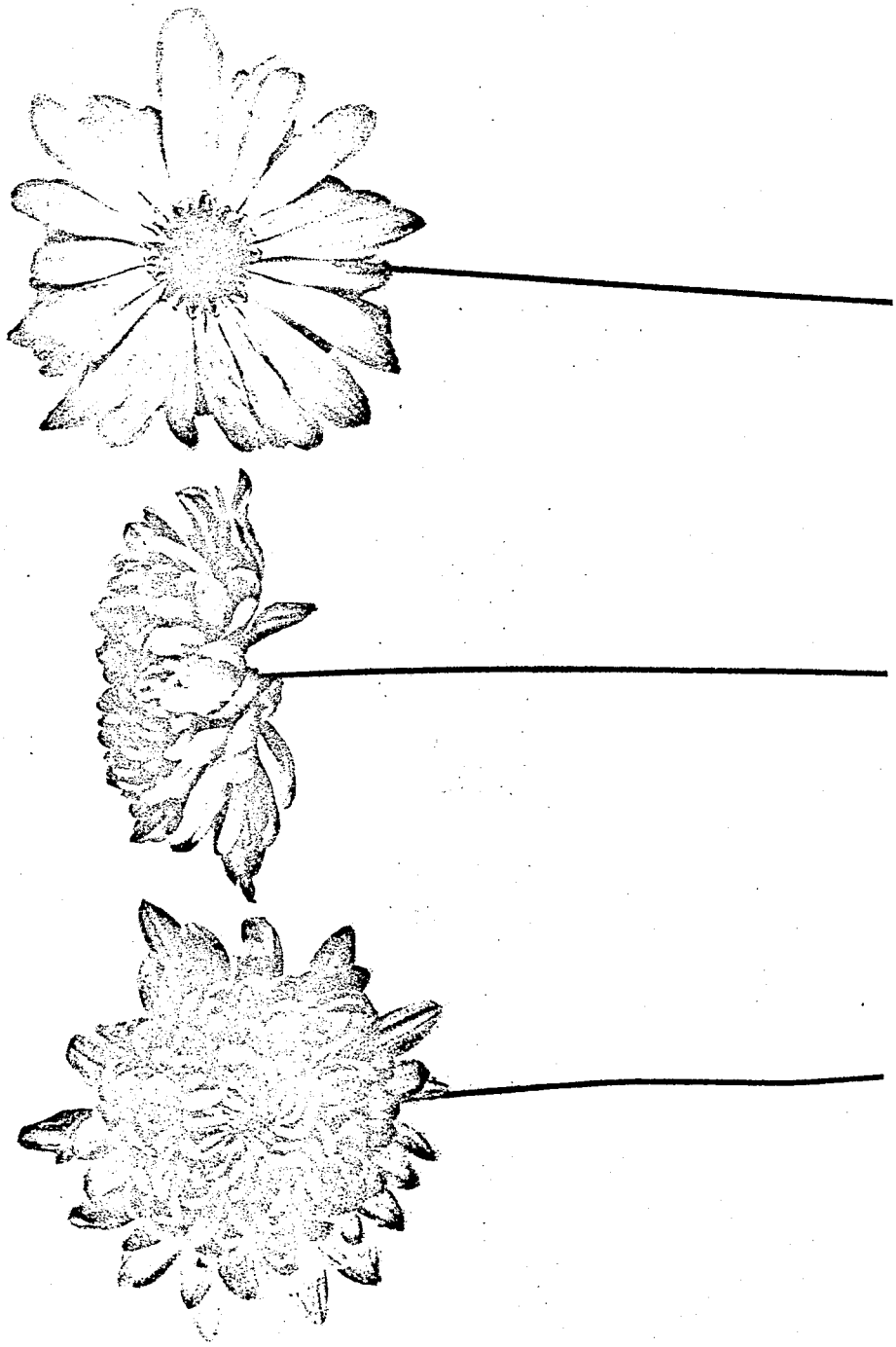

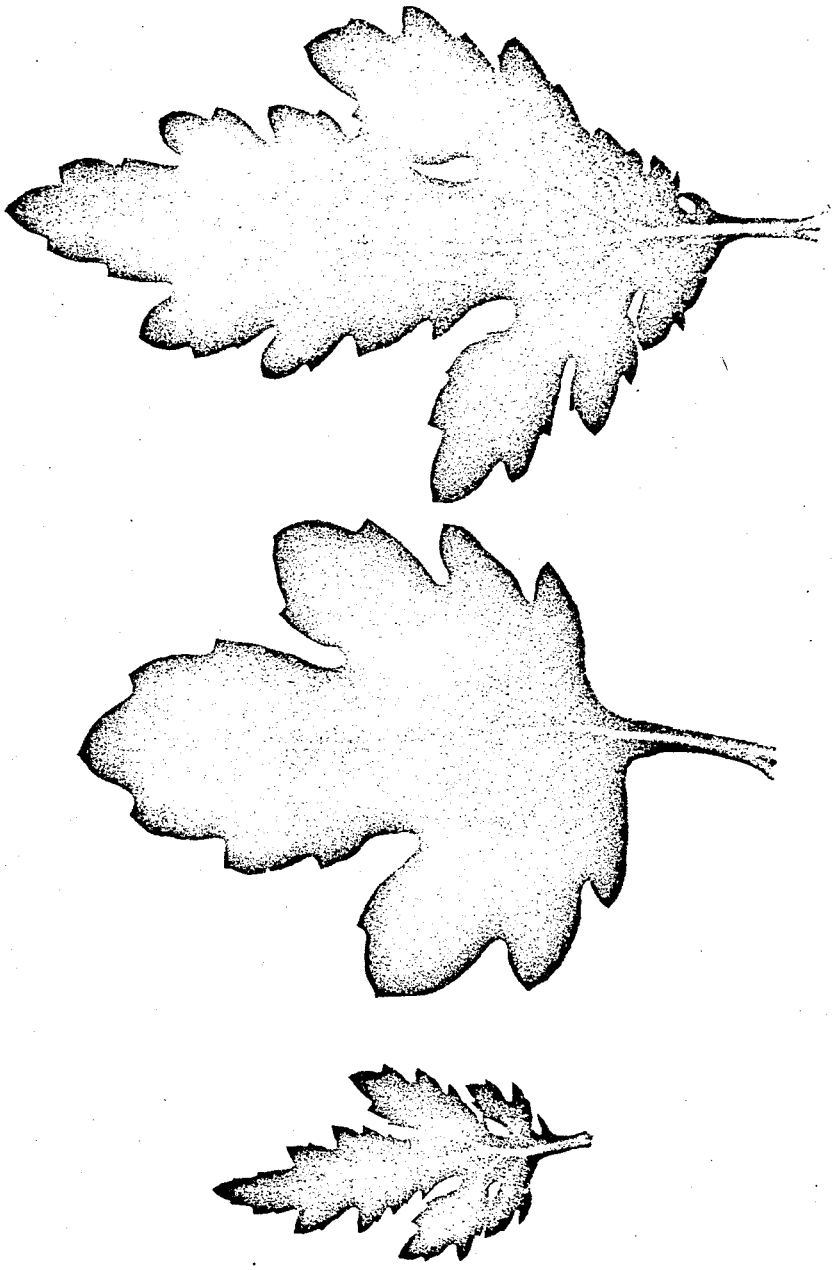

* * * * *